United States Patent

Folestad et al.

(10) Patent No.: US 6,633,792 B1
(45) Date of Patent: Oct. 14, 2003

(54) METHOD FOR CONTROLLING A COATING PROCESS

(75) Inventors: Staffan Folestad, Västra Frölunda (SE); Ingela Niklasson Björn, Göteborg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/380,937

(22) PCT Filed: Jul. 7, 1999

(86) PCT No.: PCT/SE99/01096

§ 371 (c)(1),
(2), (4) Date: Sep. 9, 1999

(87) PCT Pub. No.: WO00/03229

PCT Pub. Date: Jan. 20, 2000

(30) Foreign Application Priority Data

Jul. 13, 1998 (SE) ............................................. 9802537

(51) Int. Cl.[7] ............................................. G06F 19/00
(52) U.S. Cl. ........................................ 700/109; 424/458
(58) Field of Search ................. 700/109, 110; 424/458; 250/341.2, 341.8

(56) References Cited

U.S. PATENT DOCUMENTS

| 4,472,960 | A | * | 9/1984 | Motoyama et al. ............... 73/7 |
| 4,957,745 | A | * | 9/1990 | Jonsson et al. ............... 424/461 |
| 5,046,846 | A | * | 9/1991 | Ray et al. .................... 356/326 |
| 5,130,171 | A |   | 7/1992 | Prud'Homme et al. 427/213.36 |
| 5,170,056 | A | * | 12/1992 | Berard et al. ............. 250/341.2 |
| 5,750,996 | A | * | 5/1998 | Drennen, III et al. ... 250/341.2 |
| 5,900,633 | A | * | 5/1999 | Solomon et al. ....... 250/339.08 |
| 6,162,465 | A | * | 12/2000 | Folestad et al. ............ 424/458 |

FOREIGN PATENT DOCUMENTS

| GB | 2150692 | 7/1985 |
| WO | 9722872 | 6/1997 |

* cited by examiner

*Primary Examiner*—Leo Picard
*Assistant Examiner*—Zoila Cabrera
(74) *Attorney, Agent, or Firm*—White & Case LLP

(57) ABSTRACT

This invention relates to a method for controlling the process of manufacturing a coating of a pharmaceutical product, comprising the steps of:

performing a spectroscopic measurement on the coating;

generating a sample vector of measurement values from the spectrometric measurement;

condensing the measurement values into at least one principal parameter;

comparing the principal parameter to a predetermined corresponding model parameter;

determining deviations of the principal parameter from the corresponding model parameter and extracting information directly related to the quality of the coating; and controlling the process on the basis, at least partly, of the extracted information.

20 Claims, 1 Drawing Sheet

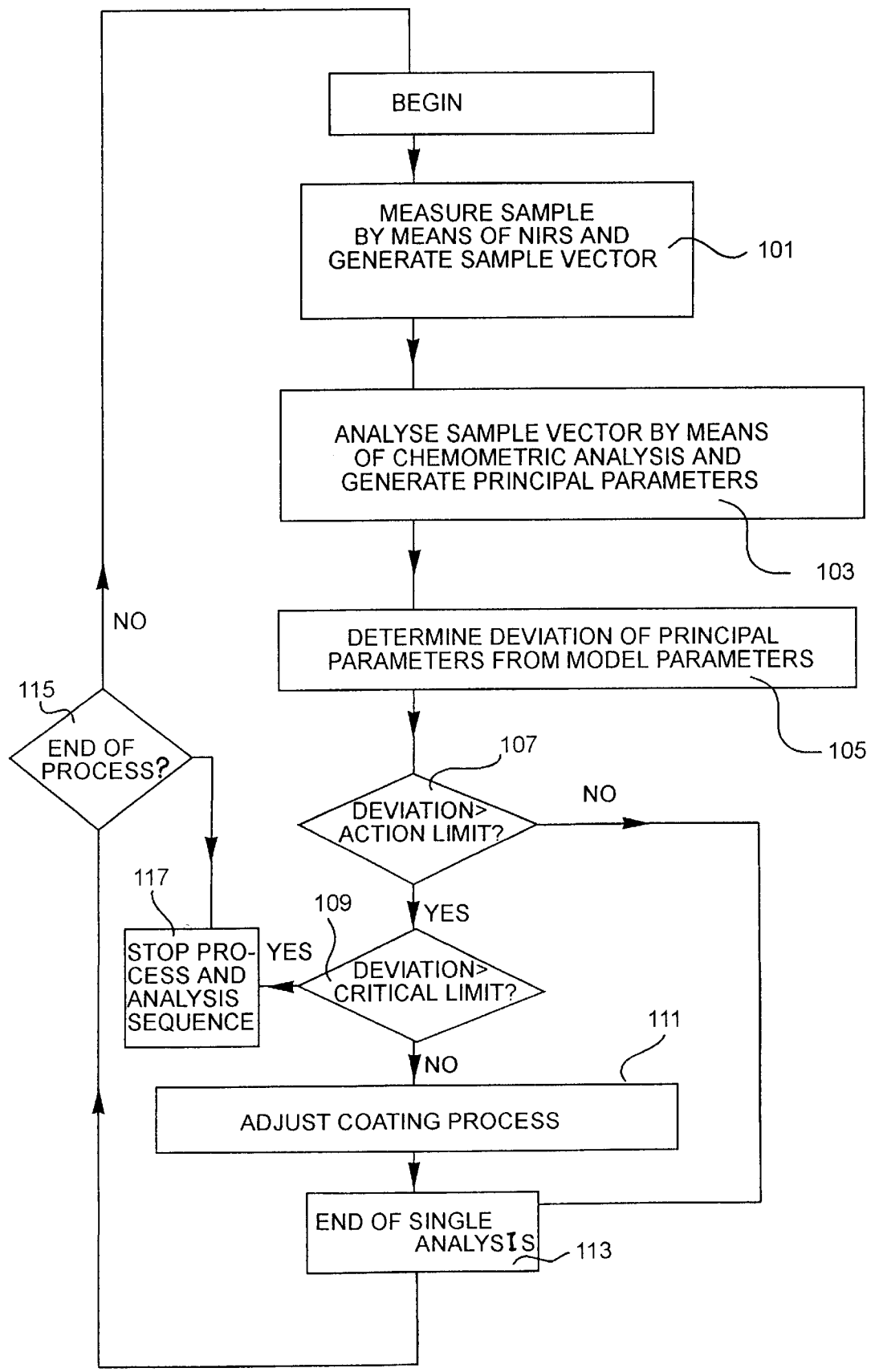

METHOD FOR CONTROLLING A COATING PROCESS

TECHNICAL FIELD

The present invention relates to a method for controlling the process of manufacturing a coating of a pharmaceutical product, such as a pellet, a tablet or a capsule.

TECHNICAL BACKGROUND

Generally, a coating of a pharmaceutical product consists of one or more films and each film consists of one or more layers. Below, "coating" is used as a comprehensive expression encompassing everything from an individual layer to a combination of several different films. Each film is the result of a single coating step, generally performed in a coating vessel, where for instance layers of the film are built up. The coating process takes place either in a fluidized bed wherein nuclei are sprayed with a specific coating mixture or by passing the nuclei through a spray dust of said mixture. Several other generally used coating techniques are known in the prior art, such as melting, aggregation etc. The total process of manufacturing a complete coating may involve a plurality of such coating steps. However, the process may as well be sequential, whereby the whole process represents a continuous flow.

Pharmaceutical products are coated for several reasons. A protective coating normally protects the active ingredients from possible negative influences from the environment, such as for example light and moisture but also temperature and vibrations. By applying such a coating the active substance is protected during storage and transport. A coating could also be applied to make the product easier to swallow, to provide it with a pleasant taste or for identification of the product. Further, coatings are applied which perform a pharmaceutical function such as conferring enteric and/or controlled release. The purpose of a functional coating is to provide a pharmaceutical preparation or formulation with desired properties to enable the transport of the active pharmaceutical substance through the digestive system to the region where it is to be released and/or absorbed. A desired concentration profile over time of the active substance in the body may be obtained by such a controlled course of release. An enteric coating is used to protect the product from disintegration in the acid environment of the stomach. Moreover, it is important that the desired functionalities are constant over time, i.e. during storage. By controlling the quality of the coating, the desired functionalities of the final product may also be controlled.

There are strict requirements from the different Registration Authorities on pharmaceutical products. These requirements will put high demands on the quality of the coating and require that the complex properties of the coating will be kept within narrow limits. In order to meet these demands, there is a need for accurate control of the coating process. Further, to be able to control the coating process; the quality of the coating should be measured directly.

The quality of the coating depends on several parameters related to physical and/or chemical properties of the coating. These principal parameters can be any of the following: chemical composition, local inhomogeneities, physical and chemical homogenity, density, mechanical properties, static parameters, modulus, tensile strength, elongation at break, compression, ductility, viscoelastic parameters, morphology, macro- and microscopic properties, amorphous and/or crystallinity, permeability, porosity, aggregation, wettability, degree of coalescence/maturity, stability and ability to resist chemical and/or physical degradation. In addition to the parameters listed above there are also other parameters not listed here. The quality of the coating affects to a great extent the release properties and has a significant impact on the storage stability. In order to keep the quality of the coating within the desired narrow limits, it is necessary to control the manufacturing process of the coating accurately.

In order to enable this accurate control, it is desired to continuously and directly evaluate the quality of the coating throughout the coating process. The present invention provides for an accurate control of a coating process for manufacturing a coating of a pharmaceutical product, which fulfills the requirements of the quality of the coating.

In a prior art method for controlling the process of manufacturing a coating, the quality of the coating is evaluated indirectly, i.e. through the release properties and the storage stability of the product. The release properties are determined by taking product samples and subjecting the samples to an environment simulating the digestive system of a human body. The amount of released active substance versus time is then measured. In order to evaluate the storage stability, the product is stored for a predetermined period of time under either established normal or accelerated conditions, whereafter, a measurement is performed on the product. An accelerated condition is typically characterized by high to temperature (30–100° C.) and/or high humidity. If the results are unsatisfactory, the coating process is analysed, leading to adjustments of the raw materials or of the relation between components of the mixture used for the coating. Other adjustments of the manufacturing process could also be a consequence of this evaluation process. These measurements and adjustments are repeated on subsequently manufactured products, until the measured release properties and/or storage stability properties are in accordance with the desired properties.

The above described prior art method for controlling the quality of the coating is slow, i.e. the time period lapsed from the manufacture of the product until it is determined whether the product is usable or not is long. Moreover, the process of starting up a new manufacturing line, the scaling up of an existing manufacturing process, manifolding an existing manufacturing line, etc., gives a prolonged adjustment phase before a production line could be run continuously producing an appropriate coating with acceptable properties. Further, these known methods to measure the quality of the coating are indirect and rough.

A main factor commonly adjusted in order to correct the release properties is the thickness of the coating. In order to determine the thickness of the coating, the product is weighed before and after the actual coating process and the difference is determined. The difference of weight provides a rough measurement value of the thickness of the coating. This measurement value is merely a mean value of the coating thickness of an entire batch and is not fully reliable to use as a base for adjusting a manufacturing quality, i.e. the quality of the process itself but also the quality of the final product. The indirect measurements cause an additional problem. Quality variations acting disadvantageously on the product properties during storage may not be detected by means of the prior art release profile measurement. Consequently, the deteriorated release properties are not detected until after having stored the products. This causes an extremely long adjustment phase. Thus, there is also a need for a faster way to determine the storage stability of the product, in order to be able to significantly shorten the adjustment phase.

Hence, there is a great demand for improved techniques for measuring and controlling the quality of the coating in a process for manufacturing a pharmaceutical product.

SUMMARY OF THE INVENTION

The object of the present invention is to provide a method for controlling the process of manufacturing a coating of a pharmaceutical product, which method overcomes the above mentioned drawbacks of prior art, and significantly reduces the time for said adjustment phase.

The object is achieved by a method for controlling the process of manufacturing a coating of a pharmaceutical product, in accordance with the present invention. The method set out in claim 1 comprises the steps of:

performing a spectrometric measurement on said coating;

generating a sample vector of measurement values from said spectrometric measurement;

condensing said measurement values into at least one principal parameter, comparing said at least one principal parameter to a predetermined corresponding model parameter;

determining deviations of said at least one principal parameter from said corresponding model parameter and extracting information directly related to the quality of said coating; and controlling the process on the basis, at least partly, of said information.

The steps of performing a spectrometric measurement on the coating, generating a sample vector of measurement values and condensing said measurement values provide information directly related to the physical and/or chemical properties of the coating. These properties constitute to a great extent the quality of the coating. Thus, in accordance with this method, the quality of the coating is measured directly and the control of the manufacturing process is based, at least partly, on that measurement.

The method according to the present invention advantageously enables the control to be based on measurements of the quality of the coating of samples at any stage of the coating process. The measurements can be performed during the actual coating process, e.g. within a coating vessel or by taking out a sample from the coating vessel without interrupting or interfering with the coating process. The measurement can also be performed after the coating process, e.g. on a sample taken out of a coating vessel or on a final product.

Since the inventive employment of spectrometric measurements advantageously enables the quality of the coating analysis to be carried out in-line, i.e. in the process vessel during the manufacturing process, the present invention provides for in-line adjustments of the process. The possibility to perform in-line adjustments reduces the waste of products having properties beyond the predetermined limits.

Further objects and advantages of the present invention will become apparent from the appended claims, by the following detailed description and by means of exemplary embodiments.

BRIEF DESCRIPTION OF THE DRAWING

The drawing shows a flow diagram of an embodiment of the method according to the present invention.

DESCRIPTION OF THE EMBODIMENTS

In a preferred embodiment of the method according to the present invention; the steps disclosed in the flow diagram are performed. These steps constitute process control on the basis of a sequence of single analyses. The analyses are most often repeated over and over again during the manufacture of a batch in order to monitor and continuously adjust the process. However, sometimes a single analysis is performed.

In a first step 101, a sample is subjected to a spectrometric measurement, preferably NIRS (Near Infrared Spectrometry), resulting in a plurality of measurement values. The sample can be measured at or originate from any portion of the manufacturing line or stage of the manufacture, or coating process. The resulting values are represented in a sample vector. NIRS provides both physical and chemical properties of the coating. This spectrometric method, like several other commonly used spectrometric methods, is non-invasive as well as non-destructive. A NIRS measurement is fast and therefore, it is employable for measuring samples of all kinds including samples maintained within the coating process, as explained above. The possibilities obtained by NIRS measurements will be further discussed below.

Further, with a spectrometric measurement according to the invention, it is possible to extract information from several different depths of the sample subjected to the spectrometric measurement, i.e. from the surface as well from deeper levels of the coating. Additionally, it is possible to directly measure the thickness of the coating. The spectrometric measurement can be carried out in such a manner that the sample, the coating thickness of which is to be measured, is adjusted to a desired level. Thus, on the contrary to the method described in the prior art, the mean coating thickness or a variation of the coating thickness can be measured, for example, on a dose level, i.e. on a tablet or even on a sub dose level, i.e. on a pellet from a multiple unit dosage form.

In a second step 103, the sample vector is evaluated in order to extract information directly related to the quality of the coating. In the present embodiment the evaluation is performed by subjecting the sample vector to a mathematical analysis, weighting the values, in conjunction to previous values, and condensing them to at least one principal parameter describing some main features representing said information. In the present embodiment chemometric methods are used. More particularly and at least in the case of continuously measuring samples during the coating, a multivariate analysis, such as PCA (Principal Component Analysis), or PLS (Partial Least Squares) is performed on the sample vector.

Then, in a step shown as 105, the extracted principal parameters are compared to predetermined corresponding model parameters. The model parameters represent known quality features related to a specific physical and/or chemical structure, which in turn causes for example specific release properties. The model parameters are predetermined by analyzing quality features from a large amount of test batches. The quality features also comprise quality features related to other properties of interest, such as the storage stability of the end products. The deviations of the extracted parameters from the model parameters are evaluated.

In a step 107, it is determined whether the deviation of any parameter exceeds a first predetermined limit, the so-called action limit. If not, the method is continued in a step shown as step 113, but if the action limit is exceeded the method is continued in a step 109.

In step 109, it is determined whether the deviation of the parameter(s) that exceeded the action limit also exceeds a second limit, the so-called critical limit. If the critical limit is exceeded, the method is continued in a step 117, where the process and analysis sequence are stopped. Within the range between the action limit and the critical limit the coating process needs to be adjusted. If the critical limit is not exceeded, the method is continued in a step 111 for adjustment of the coating process. The adjustment is performed in accordance with the parameter(s) exceeding the action limit and in relation to the magnitude of the deviation. The adjustment is further performed as a feedback control applied to the conditions within the coating vessel. Then, the method is continued in step 113.

However, if any principal parameter or a specified number or set of principal parameters exceeds the critical limit that indicates a disturbance in the coating process, the coating process and analysis sequence then ought to be stopped. Such a disturbance might indicate a detrimental defect that should be investigated by an operator.

In step 113, the single analysis is ended, and the method is continued in a step 115. In step 115, it is determined whether the process is finished and should be stopped. If the answer is yes, the process is stopped in step 117, and so is the analysis sequence. If, on the other hand, the answer is no, the sequence of analysis is continued.

As described above, in accordance with the method of this invention it is possible to directly measure the quality of the coating, in terms of parameters related to the quality of the coating according to the parameters listed on page 2. The measurements may be used for controlling, in a predictable and controlled manner, not only the thickness of the coating but also different variables affecting the quality of the coating, such as concentrations of components and humidity or temperature in the environment where the products are coated. Further, this may be done by applying the method of the present invention to different stages of the coating process.

The basic application is to extract enough information about the coating at every stage during the coating process in order to be able to control the coating process accurately. The method according to the present invention could be used as a replacement for the prior art analysis based on and delimited to measuring the release rate in a simulated digestive system, but more often it could be used as a complement to said prior art analysis by adding information related to the quality of the coating. This information related to the quality of the coating is not directly obtainable by any prior art method. It is to be noted that the information related to the quality of the coating includes information related to storage stability which makes it possible to omit the storage stability test used in prior art methods when this is required. The results are then used to adjust the coating process accordingly.

It is to be emphasized that the method according to the invention is applicable to the process during the actual running of the coating process. By performing measurements on samples taken out from within the coating process or even performing measurements on samples during the coating process within the coating vessel, the coating process could be continuously monitored. Since the method is fast it is possible to control the growth of the coating in accordance with the results of the measurements. Thus, an instant feedback affecting the same line to which the samples belong could be obtained.

In the methods frequently used in the prior art, the process parameters according to performed analyses are set once and for all after having obtained satisfactory properties by adjustments. This does however not guarantee an accurate batch to batch quality of the end product. For example, the quality of the raw material may vary between different deliveries; the environment within the coating vessel may vary over time, etc. These variations may affect the quality of the product significantly. By the continuous monitoring process according to the present invention it is possible to detect and immediately correct any variations resulting in fewer variations of product quality and makes it possible to minimize the waste of material and final products.

In another embodiment of the method according to the present invention a step of prediction is added. The forming of the coating can be interpreted as a drying process. The drying velocity is dependent on driving forces, available area, diffusion, and the combination of materials and type of coating. The driving force could be expressed as a difference in vapor pressures, temperatures, concentrations, relative humidity, etc. Consequently, for example, the drying velocity could be expressed as follows:

$$\frac{dm}{dt} = K_G \cdot A \cdot (P_{saturation} - P_{air}) \qquad \text{eq. (1)}$$

where $K_G$ is the diffusion constant for vapor in air, A is the available area and the expression in brackets represent the difference in vapor pressures.

It will be understood by a person skilled in the art that the equation above can be modified in any different way according to changed or different manufacturing process properties, i.e. process vessel properties.

In a performed experiment, the quality of the coating was predicted for different drying velocities, and then compared to samples having known desired characteristics. The prediction was well correlated to the samples.

By initially predicting the drying velocity on the basis of the desired quality of the coating and setting initial process parameters in accordance with said prediction, i.e. in order to obtain the predicted drying velocity, the adjustment phase is further reduced so that merely fine adjustments remain. For example, the drying velocity is well correlated to the release properties as well as to the storage stability, and, thus, process control in order to achieve desired release properties and storage stability is facilitated by this prediction.

Then during the manufacture of the coating, the drying velocity is measured in accordance with this embodiment of the method and the process is adjusted accordingly.

In order to predict the drying velocity, a model of the environment within the coating vessel is needed. When, for example, the size or form of the vessel is changed during scaling up of the process, the environment is likely to change. Conventionally, that would lead to time consuming measurements and adjustments in order to regain the same coating properties. By employing the present method, i.e. the possibility to measure the drying velocity, the adjustment phase is significantly simplified.

In addition to the above embodiments further modifications are possible within the scope of the invention as defined by the enclosed claims.

Examples of possible modifications comprise for example the use of other spectrometric methods, such as those based on Raman scattering, or absorption in the UV and visible or infra-red (IR) wavelength regions or luminescence such as fluorescence emission.

Alternative embodiments of the present method comprise different combinations of more than one spectrometric or non-spectrometric methods, and also combinations of one or more spectrometric methods and one or more prior art methods.

Another example of a modification substitutes a more simple analysis to the chemometric methods as follows.

Generally, when using spectrometric methods, broad response spectra are obtained. However, instead of analyzing all of the measurement values obtained over such a broad response spectrum by applying chemometric methods, merely one or a few values of the measurement values are analyzed. For example, the measurement values at a few individual frequencies could be analyzed. Also, when employing Raman spectrometry, which often results in values well separated by wavelength, this simplified analysis can be useful.

Finally, it is to be noted that the method of the present invention is applicable irrespective of what coating technique is employed.

What is claimed is:

1. A method for controlling the process of manufacturing a coating of a pharmaceutical product, wherein the method comprises monitoring simultaneously principal parameters relating to properties of the coating by performing the following steps comprising:
   (a) performing a spectrometric measurement on said coating;
   (b) generating a sample vector of a plurality of measurement values from said spectrometric measurement;
   (c) condensing said measurement values into principal parameters relating to properties of the coating;
   (d) comparing said principal parameters to predetermined corresponding model parameters;
   (e) determining deviations of said principal parameters from said corresponding model parameters and extracting information directly related to the quality of said coating; and
   (f) controlling the process at least partly on the basis of said information by applying instant feedback control to the process in relation to the magnitude of the deviation of said principal parameters.

2. The method according to claim 1, wherein at least one principal parameter relates to physical properties of the coating.

3. The method according to claim 1, wherein at least one principal parameter relates to chemical properties of the coating.

4. The method according to claim 1, wherein at least one principal parameter relates to physical and chemical properties of the coating.

5. The method according to any one of claims 2–4, wherein at least one principal parameter corresponds to the permeability of the coating.

6. The method according to any one of claims 2–4, wherein at least one principal parameter corresponds to mechanical properties of the coating.

7. The method according to any one of claims 2–4, wherein at least one principal parameter corresponds to the stability of the coating.

8. The method according to claim 1, wherein the sample vector comprises a single measurement value.

9. The method according to claim 1, wherein the step of performing a measurement on said coating is carried out on a sample at any stage of the coating process.

10. The method according to claim 1, wherein the step of performing a measurement on said coating is carried out on a sample within a coating vessel during the actual coating process.

11. The method according to claim 1, wherein the step of performing a measurement on the coating is carried out on a final product in order to determine the quality of the coating.

12. The method according to claim 1, wherein the step of controlling the process comprises feedback control applied to the conditions within said coating vessel.

13. The method according to claim 1, wherein said spectrometric measurement is performed by means of near-infrared spectrometry.

14. The method according to claim 1, wherein said spectrometric measurement is performed by means of a spectrometric method based on Raman scattering.

15. The method according to claim 1, wherein said spectrometric measurement is performed by means of one of the spectrometric methods selected from the group consisting of: luminescence, fluorescence emission, and absorption in the UV, visible, or infra-red (IR) wavelength regions.

16. The method according to claim 1, further comprising the initial steps of:
   predicting a drying velocity on the basis of a desired quality of the coating; and
   setting initial parameters of the process accordingly.

17. The method according to claim 1, wherein the step of performing a measurement on said coating comprises the step of measuring the coating by means of a plurality of spectrometric measurements, each based on a different spectrometric method.

18. The method according to claim 1, wherein the step of performing a measurement on said coating comprises the further step of measuring the coating by means of a non-spectrometric method.

19. A pharmaceutical product comprising a coating, the coating applied by a method controlled by a process comprising the steps of:
   (a) performing a spectrometric measurement on said coating;
   (b) generating a sample vector of a plurality of measurement values from said spectrometric measurement;
   (c) condensing said measurement values into principal parameters relating to properties of the coating;
   (d) comparing said principal parameters to predetermined corresponding model parameters;
   (e) determining deviations of said principal parameters from said corresponding model parameters and extracting information directly related to the quality of said coating; and
   (f) controlling the process at least partly on the basis of said information by applying instant feedback control to the process in relation to the magnitude of the deviation of said principal parameters.

20. A method for controlling the process of manufacturing a coating of a pharmaceutical product, wherein the method comprises monitoring simultaneously principal parameters relating to properties of the coating by performing the following steps comprising:
   (a) performing a spectrometric measurement on said coating;
   (b) generating a sample vector of a plurality of measurement values from said spectrometric measurement;
   (c) condensing said measurement values into principal parameters relating to properties of the coating;
   (d) comparing said principal parameters to predetermined corresponding model parameters;
   (e) determining deviations of said principal parameters from said corresponding model parameters and extracting information directly related to the quality of said coating; and
   (f) adjusting the process at least partly on the basis of said information by applying instant feedback control to the process in relation to the magnitude of the deviation of said principal parameters.

* * * * *